US012285160B2

(12) United States Patent
Walters et al.

(10) Patent No.: US 12,285,160 B2
(45) Date of Patent: *Apr. 29, 2025

(54) MULTI-LUMEN TAMPER TUBE

(71) Applicant: Teleflex Life Sciences LLC, Wilmington, DE (US)

(72) Inventors: Greg Alan Walters, Exton, PA (US); Samuel Nardone, Exton, PA (US)

(73) Assignee: Teleflex Life Sciences LLC, Wilmington, DE (US)

( * ) Notice: Subject to any disclaimer, the term of this patent is extended or adjusted under 35 U.S.C. 154(b) by 738 days.

This patent is subject to a terminal disclaimer.

(21) Appl. No.: 17/476,877

(22) Filed: Sep. 16, 2021

(65) Prior Publication Data

US 2022/0000463 A1   Jan. 6, 2022

Related U.S. Application Data

(63) Continuation of application No. 16/522,161, filed on Jul. 25, 2019, now Pat. No. 11,123,053, which is a (Continued)

(51) Int. Cl.
*A61B 17/00* (2006.01)
*A61M 39/00* (2006.01)
(Continued)

(52) U.S. Cl.
CPC ......... *A61B 17/0057* (2013.01); *A61M 39/00* (2013.01); *A61B 2017/00469* (2013.01); (Continued)

(58) Field of Classification Search
CPC ...... A61B 17/0057; A61B 2017/00469; A61B 2017/00623; A61B 2017/00628;
(Continued)

(56) References Cited

U.S. PATENT DOCUMENTS

| 3,125,095 A | 3/1964 | Kaufman et al. |
| 4,665,918 A | 5/1987 | Garza et al. |

(Continued)

FOREIGN PATENT DOCUMENTS

| EP | 0474752 B1 | 6/1995 |
| EP | 0766947 A2 | 4/1997 |

(Continued)

OTHER PUBLICATIONS

European Search Report and Search Opinion mailed May 10, 2023, in EP Patent Application No. 23153276.3.

(Continued)

*Primary Examiner* — Jason E Flick
(74) *Attorney, Agent, or Firm* — Dorsey & Whitney LLP

(57) ABSTRACT

The present technology relates generally to devices and methods for closing percutaneous punctures, and more particularly to a multi-lumen tamper for such a device. A vascular closure device for sealing a percutaneous puncture in a wall of a body passageway is disclosed, the vascular closure device including a plug configured to engage a surface of the puncture; a suture configured coupled to the plug; a locking member configured to engage the plug; and a tamper comprising a first lumen and a second lumen.

20 Claims, 13 Drawing Sheets

Related U.S. Application Data continuation of application No. 15/675,115, filed on Aug. 11, 2017, now Pat. No. 10,390,810, which is a continuation of application No. 13/946,398, filed on Jul. 19, 2013, now Pat. No. 9,757,104.

(60) Provisional application No. 61/673,570, filed on Jul. 19, 2012.

(51) Int. Cl.
  *A61B 17/04* (2006.01)
  *A61B 90/00* (2016.01)
  *A61M 39/08* (2006.01)

(52) U.S. Cl.
  CPC ............ *A61B 2017/00623* (2013.01); *A61B 2017/00628* (2013.01); *A61B 2017/0496* (2013.01); *A61B 90/39* (2016.02); *A61B 2090/3966* (2016.02); *A61M 2039/082* (2013.01)

(58) Field of Classification Search
  CPC .... A61B 2017/0496; A61B 2090/3966; A61B 90/39; A61M 39/00; A61M 2039/082
  See application file for complete search history.

(56) References Cited

U.S. PATENT DOCUMENTS

| | | |
|---|---|---|
| 4,760,847 A | 8/1988 | Vaillancourt |
| 4,798,594 A | 1/1989 | Hillstead |
| 4,890,612 A | 1/1990 | Kensey |
| 4,895,346 A | 1/1990 | Steigerwald |
| 4,895,565 A | 1/1990 | Hillstead |
| 4,990,151 A | 2/1991 | Wallsten |
| 5,021,059 A | 6/1991 | Kensey et al. |
| 5,026,377 A | 6/1991 | Burton et al. |
| 5,041,095 A | 8/1991 | Littrell |
| 5,059,183 A | 10/1991 | Semrad |
| 5,222,974 A | 6/1993 | Kensey et al. |
| 5,282,827 A | 2/1994 | Kensey et al. |
| 5,292,309 A | 3/1994 | Tassel et al. |
| 5,306,254 A | 4/1994 | Nash et al. |
| 5,322,508 A | 6/1994 | Viera |
| 5,324,306 A | 6/1994 | Makower et al. |
| 5,360,414 A | 11/1994 | Yarger |
| 5,363,847 A | 11/1994 | Viera |
| 5,411,520 A | 5/1995 | Nash et al. |
| 5,531,759 A | 7/1996 | Kensey et al. |
| 5,545,178 A | 8/1996 | Kensey et al. |
| 5,643,318 A | 7/1997 | Tsukernik et al. |
| 5,662,681 A | 9/1997 | Nash et al. |
| 5,700,277 A | 12/1997 | Nash et al. |
| 5,702,421 A | 12/1997 | Schneidt |
| 5,843,124 A | 12/1998 | Hammerslag |
| 6,010,520 A | 1/2000 | Pattison |
| 6,056,768 A | 5/2000 | Cates et al. |
| 6,090,130 A | 7/2000 | Nash et al. |
| 6,107,004 A | 8/2000 | Donadio, III |
| 6,179,863 B1 | 1/2001 | Kensey et al. |
| 6,245,054 B1 | 6/2001 | Fuimaono et al. |
| 6,425,911 B1 | 7/2002 | Akerfeldt et al. |
| 6,440,151 B1 | 8/2002 | Cragg et al. |
| 6,440,153 B2 | 8/2002 | Cragg et al. |
| 6,447,534 B2 | 9/2002 | Cragg et al. |
| 6,494,848 B1 | 12/2002 | Sommercorn et al. |
| 6,682,489 B2 | 1/2004 | Tenerz et al. |
| 6,860,895 B1 | 3/2005 | Akerfeldt et al. |
| 7,037,322 B1 | 5/2006 | Sing et al. |
| 7,044,916 B2 | 5/2006 | Tenerz et al. |
| 7,073,509 B2 | 7/2006 | Tenerz et al. |
| 7,094,209 B2 | 8/2006 | Egnelöv et al. |
| 7,285,097 B2 | 10/2007 | Tenerz et al. |
| 7,316,704 B2 | 1/2008 | Bagaoisan et al. |
| 7,597,705 B2 | 10/2009 | Forsberg et al. |
| 7,618,436 B2 | 11/2009 | Forsberg |
| 7,648,493 B2 | 1/2010 | Forsberg et al. |
| 7,695,493 B2 | 4/2010 | Saadat et al. |
| 7,850,654 B2 | 12/2010 | Belhe et al. |
| 7,905,902 B2 | 3/2011 | Huitema et al. |
| 8,029,533 B2 | 10/2011 | Bagaoisan et al. |
| 8,097,007 B2 | 1/2012 | Evans et al. |
| 8,137,321 B2 | 3/2012 | Argentine |
| 8,273,094 B2 | 9/2012 | Belhe et al. |
| 8,337,522 B2 | 12/2012 | Ditter |
| 8,382,793 B2 | 2/2013 | Egnelöv et al. |
| 8,435,256 B2 | 5/2013 | Lehe et al. |
| 8,444,673 B2 | 5/2013 | Thielen et al. |
| 8,540,750 B2 | 9/2013 | Tegels |
| 8,685,059 B2 | 4/2014 | Walters |
| 8,870,917 B2 | 10/2014 | Walters |
| 8,926,564 B2 | 1/2015 | King et al. |
| 8,974,476 B2 | 3/2015 | Tegels |
| 9,089,363 B2 | 7/2015 | Dooney et al. |
| 9,675,371 B2 | 6/2017 | Shimon |
| 9,757,104 B2 | 9/2017 | Walters et al. |
| 10,154,835 B2 | 12/2018 | Walters et al. |
| 10,383,611 B2 | 8/2019 | Walters et al. |
| 10,390,810 B2 | 8/2019 | Walters et al. |
| 10,448,937 B2 | 10/2019 | Walters et al. |
| 10,485,524 B2 | 11/2019 | Walters et al. |
| 10,555,727 B2 | 2/2020 | Walters et al. |
| 10,639,019 B2 | 5/2020 | Walters |
| 10,668,253 B2 | 6/2020 | Jacobs |
| 10,682,128 B2 | 6/2020 | Walters et al. |
| 11,020,224 B2 | 6/2021 | Jacobs |
| 11,123,053 B2 | 9/2021 | Walters et al. |
| 11,419,592 B2 | 8/2022 | Walters et al. |
| 11,576,663 B2 | 2/2023 | Walters et al. |
| 11,589,855 B2 | 2/2023 | Walters et al. |
| 11,779,320 B2 | 10/2023 | Walters et al. |
| 2001/0003158 A1 | 6/2001 | Kensey et al. |
| 2001/0044639 A1 | 11/2001 | Levinson |
| 2002/0022822 A1 | 2/2002 | Cragg et al. |
| 2003/0078616 A1 | 4/2003 | Ginn et al. |
| 2004/0138674 A1 | 7/2004 | Egnelov et al. |
| 2004/0147950 A1 | 7/2004 | Mueller et al. |
| 2004/0204741 A1 | 10/2004 | Egnelov et al. |
| 2004/0267308 A1 | 12/2004 | Bagaoisan et al. |
| 2005/0085856 A1 | 4/2005 | Ginn |
| 2005/0107820 A1 | 5/2005 | Forsberg et al. |
| 2005/0107826 A1 | 5/2005 | Zhu et al. |
| 2005/0107827 A1 | 5/2005 | Paprocki |
| 2005/0125030 A1 | 6/2005 | Forsberg et al. |
| 2005/0277961 A1 | 12/2005 | Stone et al. |
| 2006/0058844 A1 | 3/2006 | White et al. |
| 2006/0217664 A1 | 9/2006 | Hattler et al. |
| 2006/0229673 A1 | 10/2006 | Forsberg |
| 2007/0123936 A1 | 5/2007 | Goldin et al. |
| 2007/0282373 A1 | 12/2007 | Ashby et al. |
| 2008/0082123 A1* | 4/2008 | Forsberg ............ A61B 17/0057 606/214 |
| 2008/0157017 A1 | 7/2008 | Macatangay et al. |
| 2008/0306509 A1 | 12/2008 | Osborne |
| 2009/0054926 A1* | 2/2009 | Pipenhagen ....... A61B 17/0057 606/213 |
| 2009/0088793 A1 | 4/2009 | Bagaoisan et al. |
| 2009/0099598 A1 | 4/2009 | McDevitt et al. |
| 2009/0137870 A1 | 5/2009 | Bakos et al. |
| 2009/0171387 A1 | 7/2009 | Pipenhagen et al. |
| 2009/0248064 A1 | 10/2009 | Preinitz |
| 2009/0312790 A1 | 12/2009 | Forsberg et al. |
| 2009/0318894 A1 | 12/2009 | Lafitte et al. |
| 2010/0016887 A1 | 1/2010 | Inderbitzi |
| 2010/0168789 A1 | 7/2010 | Bagaoisan et al. |
| 2010/0179589 A1 | 7/2010 | Roorda et al. |
| 2010/0185216 A1 | 7/2010 | Garrison et al. |
| 2011/0004162 A1 | 1/2011 | Tal |
| 2011/0046665 A1 | 2/2011 | Green et al. |
| 2011/0054456 A1 | 3/2011 | Thompson et al. |
| 2011/0160765 A1 | 6/2011 | Melmed et al. |
| 2011/0208222 A1 | 8/2011 | Fjahnicky et al. |
| 2011/0213414 A1 | 9/2011 | McGuckin, Jr. et al. |
| 2011/0213415 A1 | 9/2011 | McGuckin, Jr. et al. |

(56) References Cited

U.S. PATENT DOCUMENTS

| | | |
|---|---|---|
| 2011/0301619 A1 | 12/2011 | Walters |
| 2012/0010634 A1 | 1/2012 | Crabb et al. |
| 2012/0022585 A1 | 1/2012 | Atanasoska et al. |
| 2012/0065668 A1 | 3/2012 | Ginn et al. |
| 2012/0071919 A1 | 3/2012 | Pipenhagen et al. |
| 2012/0083829 A1 | 4/2012 | Ginn et al. |
| 2012/0101525 A1 | 4/2012 | Jenson et al. |
| 2012/0109192 A1 | 5/2012 | Egnelöv et al. |
| 2012/0116446 A1 | 5/2012 | Green et al. |
| 2012/0143244 A1 | 6/2012 | Hill et al. |
| 2012/0143245 A1 | 6/2012 | Tegels |
| 2012/0143249 A1 | 6/2012 | Jenson et al. |
| 2012/0158044 A1 | 6/2012 | Jenson et al. |
| 2012/0165854 A1 | 6/2012 | Pipenhagen et al. |
| 2012/0245517 A1 | 9/2012 | Tegels |
| 2012/0245597 A1 | 9/2012 | Tegels |
| 2012/0245624 A1 | 9/2012 | Glazier et al. |
| 2012/0283770 A1 | 11/2012 | Kramer et al. |
| 2012/0296275 A1 | 11/2012 | Martin et al. |
| 2013/0006297 A1 | 1/2013 | Drasler |
| 2013/0006298 A1 | 1/2013 | Terwey |
| 2013/0025588 A1 | 1/2013 | Bosel |
| 2013/0035719 A1 | 2/2013 | Hill et al. |
| 2013/0072949 A1 | 3/2013 | Halac et al. |
| 2013/0079802 A1 | 3/2013 | Halac et al. |
| 2013/0103077 A1 | 4/2013 | Ditter |
| 2013/0131718 A1 | 5/2013 | Jenson et al. |
| 2013/0144316 A1 | 6/2013 | McCrea et al. |
| 2013/0150884 A1 | 6/2013 | Belhe et al. |
| 2013/0178895 A1 | 7/2013 | Walters et al. |
| 2013/0226227 A1 | 8/2013 | Terwey |
| 2014/0039264 A1 | 2/2014 | Heiman |
| 2014/0046217 A1 | 2/2014 | Lim |
| 2014/0046220 A1 | 2/2014 | Nelson |
| 2014/0094846 A1 | 4/2014 | Lim et al. |
| 2014/0188160 A1 | 7/2014 | Tegels |
| 2014/0200611 A1 | 7/2014 | Walters |
| 2014/0222064 A1 | 8/2014 | Tegels |
| 2014/0236088 A1 | 8/2014 | Al-Rashdan et al. |
| 2014/0309686 A1 | 10/2014 | Ginn et al. |
| 2014/0364899 A1 | 12/2014 | Ginn et al. |
| 2015/0068009 A1 | 3/2015 | Walters |
| 2015/0100083 A1 | 4/2015 | Walters et al. |
| 2015/0173794 A1 | 6/2015 | Kurth et al. |
| 2016/0228109 A1 | 8/2016 | Jacobs et al. |
| 2017/0135725 A1 | 5/2017 | Tegels |
| 2017/0333015 A1 | 11/2017 | Walters et al. |
| 2019/0015204 A1 | 1/2019 | Jacobs |
| 2019/0015637 A1 | 1/2019 | Jacobs |
| 2019/0110781 A1 | 4/2019 | Walters et al. |
| 2019/0336116 A1 | 11/2019 | Walters et al. |
| 2020/0000448 A1 | 1/2020 | Walters et al. |
| 2020/0146661 A1 | 5/2020 | Walters et al. |
| 2020/0289101 A1 | 9/2020 | Walters |
| 2022/0273277 A1 | 9/2022 | Walters et al. |
| 2022/0338852 A1 | 10/2022 | Walters |

FOREIGN PATENT DOCUMENTS

| | | |
|---|---|---|
| EP | 0797953 A2 | 10/1997 |
| EP | 1163020 A1 | 12/2001 |
| EP | 1169968 A1 | 1/2002 |
| EP | 1222896 A2 | 7/2002 |
| EP | 1254634 A1 | 11/2002 |
| EP | 0664687 B2 | 8/2003 |
| EP | 1371333 A1 | 12/2003 |
| EP | 1413255 A1 | 4/2004 |
| EP | 1440661 A1 | 7/2004 |
| EP | 1532929 A1 | 5/2005 |
| EP | 1658811 A1 | 5/2006 |
| EP | 1695667 A1 | 8/2006 |
| EP | 1836967 A1 | 9/2007 |
| EP | 1836968 A1 | 9/2007 |
| EP | 2055236 A1 | 5/2009 |
| EP | 2064999 A2 | 6/2009 |
| EP | 2213247 A1 | 8/2010 |
| EP | 2215974 A2 | 8/2010 |
| EP | 1919367 B1 | 10/2011 |
| EP | 1874195 B1 | 1/2012 |
| EP | 1893100 B1 | 3/2012 |
| EP | 2227148 B1 | 4/2012 |
| EP | 1893099 B1 | 6/2012 |
| EP | 1893098 B1 | 1/2014 |
| EP | 2611366 B1 | 7/2014 |
| EP | 2605707 B1 | 10/2014 |
| EP | 1773438 B1 | 1/2017 |
| WO | 1989011301 A1 | 11/1989 |
| WO | 1990014796 A1 | 12/1990 |
| WO | 1992014396 A1 | 9/1992 |
| WO | 1993008743 A1 | 5/1993 |
| WO | 1993008746 A3 | 8/1993 |
| WO | 1994007421 A1 | 4/1994 |
| WO | 1998005259 A1 | 2/1998 |
| WO | 1999022646 A1 | 5/1999 |
| WO | 2000078226 A1 | 12/2000 |
| WO | 2003094740 A1 | 11/2003 |
| WO | 2004096056 A2 | 11/2004 |
| WO | 2005002451 A1 | 1/2005 |
| WO | 2005039387 A2 | 5/2005 |
| WO | 2005060514 A2 | 7/2005 |
| WO | 2006075228 A1 | 7/2006 |
| WO | 2006110615 A2 | 10/2006 |
| WO | 2007035187 A2 | 3/2007 |
| WO | 2008036634 A1 | 3/2008 |
| WO | 2009005722 A1 | 1/2009 |
| WO | 2009025836 A1 | 2/2009 |
| WO | 2009029914 A1 | 3/2009 |
| WO | 2009035921 A2 | 3/2009 |
| WO | 2009088440 A1 | 7/2009 |
| WO | 2009088441 A1 | 7/2009 |
| WO | 2009112930 A2 | 9/2009 |
| WO | 2010129042 A1 | 11/2010 |
| WO | 2011014244 A1 | 2/2011 |
| WO | 2011019374 A1 | 2/2011 |
| WO | 2011025529 A1 | 3/2011 |
| WO | 2011025543 A2 | 3/2011 |
| WO | 2011037635 A1 | 3/2011 |
| WO | 2011146729 A2 | 11/2011 |
| WO | 2011156498 A1 | 12/2011 |
| WO | 2012009007 A1 | 1/2012 |
| WO | 2012012641 A1 | 1/2012 |
| WO | 2012045356 A1 | 4/2012 |
| WO | 2012061486 A2 | 5/2012 |
| WO | 2012064888 A2 | 5/2012 |
| WO | 2012083045 A1 | 6/2012 |
| WO | 2012145356 A1 | 10/2012 |
| WO | 2012145362 A1 | 10/2012 |
| WO | 2012148745 A1 | 11/2012 |
| WO | 2012148747 A1 | 11/2012 |
| WO | 2012158662 A1 | 11/2012 |
| WO | 2012158737 A1 | 11/2012 |
| WO | 2012158738 A1 | 11/2012 |
| WO | 2012158740 A1 | 11/2012 |
| WO | 2012158931 A1 | 11/2012 |
| WO | 2013063227 A1 | 5/2013 |
| WO | 2013081659 A1 | 6/2013 |
| WO | 2015099977 A1 | 7/2015 |
| WO | 2017123853 A1 | 7/2017 |

OTHER PUBLICATIONS

Extended European Search Report and Opinion mailed Jun. 16, 2021 in EP Application No. 21163623.8.

Extended European Search Report mailed Sep. 6, 2021 in EP Application No. 21166157.4.

International Search Report and Written Opinion for International Application No. PCT/US2012/061855 dated Jan. 22, 2013 (21 pages).

Koh, Wui-Jin et al. "Femoral vessel depth and the implications for groin node radiation," 1993, International Journal of Radiation Oncology 'Biology' Physics, vol. 27, p. 969-974.

(56) References Cited

OTHER PUBLICATIONS

Officer Gunter Held, International Search Report and the Written Opinion, International Patent Application PCT/US2017/013314, dated Apr. 18, 2017, 11 pp.
PCT International Preliminary Report on Patentability, PCT/US2014/068694, Jun. 28, 2016, 11 pp.
PCT International Search Report and the Written Opinion, PCT/US2014/068694, Mar. 17, 2015, 17 pp.
PCT International Search Report mailed Oct. 22, 2021 in PCT/US2021/041730.
PCT Written Opinion mailed Oct. 22, 2021 in PCT/US2021/041730.
Badawi et al., "A Simple Percutaneous Technique for Hemostasis and Closure after Transcatheter Aortic Valve Implantation", Catheterization and Cardiovascular Interventions, Jan. 1, 2012, 79(1), 152-155.
Bui et al., "Double-Wire Angio-Seal Closure Technique after Balloon Aortic Valvuloplasty", Catheterization and Cardiovascular Interventions, 2010, 75, 488-492.

* cited by examiner

MULTI-LUMEN TAMPER TUBE

CROSS-REFERENCE TO RELATED APPLICATIONS

This application is a continuation of U.S. application Ser. No. 16/522,161, filed Jul. 25, 2019, which is a continuation of U.S. application Ser. No. 15/675,115, filed Aug. 11, 2017, which is a continuation of U.S. application Ser. No. 13/946, 398, filed Jul. 19, 2013, now U.S. Pat. No. 9,757,104, issued Sep. 12, 2017, which claims the benefit of U.S. Provisional Patent Application No. 61/673,570 filed Jul. 19, 2012. The content of each application in the paragraph is hereby incorporated by reference herein.

TECHNICAL FIELD

The present technology relates generally to devices and methods for closing percutaneous punctures, and more particularly to a multi-lumen tamper for such a device.

BACKGROUND

Percutaneous access of the vascular system for vascular device delivery is a common medical procedure. Typically, this involves using a hollow needle to puncture a vessel, then introducing an introducer sheath to open the puncture site for the introduction of catheters and wire guides for navigation through the vascular system to facilitate delivery. For example, in many cases, vascular access requires introduction of catheters and wire guides through the femoral artery. Once the procedure is completed, the devices are removed from the patient and pressure is applied to the puncture site to stop the bleeding. Thereafter, the puncture may be sealed using a closure device.

Closure devices generally consist of three basic sealing components: a toggle (or anchor) member, a sealing member (or plug), and a filament (or suture). To lock the components together within the puncture, a locking member may be used. To facilitate sealing and locking of the closure device components within and around the puncture, a tamper may be used. Embodiments of the present technology are directed to closing percutaneous punctures using a closure device with a multi-lumen tamper.

SUMMARY

According to one aspect there is a vascular closure device for sealing a percutaneous puncture in a wall of a body passageway. The vascular closure device includes a plug configured to engage a surface of the puncture. The vascular closure device further includes a suture coupled to the plug. The vascular closure device further includes a locking member coupled to and slidable along the suture. The vascular closure device further includes a tamper slidably coupled to the suture at a location that is proximal to the locking member. The tamper has a proximal end, a distal end spaced from the proximal end along an axis, a first lumen that extends from the proximal end to the distal end along the axis, and a second lumen that extends from the proximal end to the distal end along the axis. The first lumen and the second lumen each have a cross-sectional dimension that inhibits the locking member from being pushed inside either of the first and second lumens when the tamper slides along the suture to tamp the locking member against the plug.

According to another aspect, there is a drug delivery kit, comprising: a closure device, for sealing a percutaneous puncture in a wall of a body passageway, the closure device comprising: a guidewire passing through at least a portion of the closure device; a tamper associated with the guidewire, wherein the tamper comprises at least two lumen; and a drug releasably carried in at least one of the tamper lumen.

According to another aspect, there is a deployment instrument for deploying a closure device for sealing a percutaneous puncture in a wall of a body passageway, the deployment instrument comprising: the closure device comprising a tamper, wherein the tamper comprises at least two lumen; a carrier device, wherein the carrier device is configured to hold the closure device in a pre-deployment state.

BRIEF DESCRIPTION OF THE DRAWINGS

Embodiments of the present technology are described herein with reference to the attached drawing sheets in which.

DETAILED DESCRIPTION OF ILLUSTRATIVE EMBODIMENTS

Aspects and embodiments of the present technology are directed to a method and device for closing percutaneous punctures, and more particularly to a multi-lumen tamper tube for such a device. Such devices and methods are used to close a relatively large puncture, or wound, of a body lumen, such as, for example, a femoral artery. Such a large puncture may exist as a result of balloon aortic valvuloplasty (BAV) for the treatment of aortic valve disease, a percutaneous aortic valve replacement (PAVR) procedure for the treatment of abdominal aorta disease or the like (e.g. abdominal aortic aneurysm repair, or AAA), a trans-catheter placement of stent valves for the replacement of damaged or diseased aortic valves (trans-catheter aortic valve implantation, TAVI), or any other similar related procedure (collectively herein, the "related procedures"). The multi-lumen tamper tube may be used for the precise delivery of drugs, such as thrombin, to the puncture site.

Aspects of the disclosed technology are described below with reference to a particular embodiment configured to close a percutaneous puncture in an artery of a patient. However, it should be appreciated that embodiments of the present technology may be implemented in other body lumen, including other types of vessels. Furthermore, aspects of the disclosed multi-lumen tamper are described below with reference to particular closure and deployment devices for closing percutaneous punctures. However, it should be appreciated that embodiments of the present technology may be implemented in other various closure devices.

As used herein, the term "distal" when referred to the end of an element of the present technology will refer to the end closest to, or configured to enter a puncture in, an artery of the patient, where the "proximal" end refers to the opposite end, farthest away from the artery.

Figure 1:
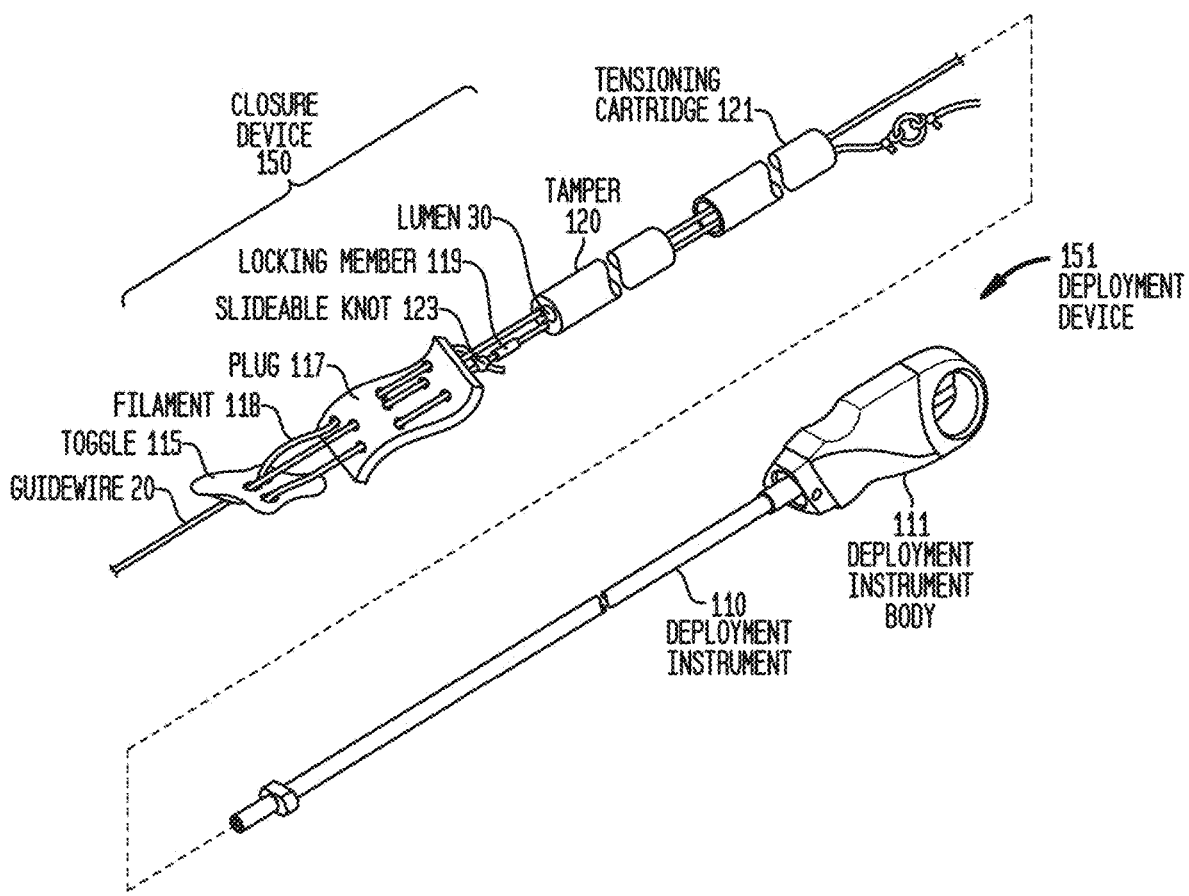
FIG. 1 is a schematic view of a closure device and deployment device, according to embodiments of the present technology.

FIG. 1 is a schematic view of a closure device 150 and deployment device 151, according to embodiments of the present technology. Prior to deployment of closure device 150, the contents of closure device 150 fit within deployment instrument 110 of deployment device 151. After deployment device 151 is inserted into the punctured artery of the patient, closure device 150 is deployed from the deployment device 151 to close the puncture. FIG. 1 shows closure device 150 in a fully deployed state.

Closure device 150 includes, among other things, a toggle 115, plug (e.g. collagen pad) 117, tamper 120 and tensioning cartridge 121. As shown in FIG. 1, toggle 115, plug 117, tamper 120 and tensioning cartridge 121 are each associated with guidewire 20. Guidewire 20 feeds through openings in toggle 115 and plug 117, and through lumen in tamper 120 and tensioning cartridge 121. Guidewire 20 serves to facilitate placement of the closure device elements around the vessel puncture during deployment of the closure device. The guidewire may also be a guidewire lumen, or in other words a guidewire with a lumen running through the guidewire along the longitudinal axis of the guidewire. The lumen of the guidewire lumen may receive another guidewire, a pharmaceutical agent or other substance, or anything else configured to feed through such a lumen. The elements of closure device 150, including toggle 115, plug 117, tamper 120, tensioning cartridge 121, and others, may be held within a release tube (not shown) or other means that is held within deployment instrument 110. The procedure of the elements of closure device 150 being held within deployment instrument 110 and released from deployment instrument 110 to close a puncture in an artery will be discussed further with respect to FIGS. 5-7.

The toggle 115 may be an elongate, low-profile member which is arranged to be seated inside the artery against the artery wall contiguous with the puncture. Toggle 115 may be constructed of a polylactic-coglycolic acid or other synthetic absorbable polymer that degrades in the presence of water into naturally occurring metabolites (e.g., water and $CO_2$). In an embodiment, the toggle 30 is a monolithic structure formed by a bio-absorbable polymer. However, a toggle may also include any other structure that is configured to be seated inside the artery against the artery wall contiguous with the puncture.

The plug 117 comprises, for example, a strip of compressible, resorbable, collagen foam. In an embodiment, the plug 117 is a collagen pad made of a fibrous collagen mix of insoluble and soluble collagen that is cross linked for strength. In an embodiment, the collagen may be obtained from the connective tissue of animals. The collagen may be purified from the subdermal layer of cowhide. Plug, or collagen, 117 expands in the presence of blood within the puncture tract.

Closure device 150 also includes suture 118. Like guidewire 20, filament 118 may also be associated with toggle 115, plug 117, tamper 120 and tensioning cartridge 121 such that filament 118 feeds through openings in toggle 115 and plug 117, and through the lumen in tamper 120 and tensioning cartridge 121. Suture 118 is, for example, a resorbable suture that is used to couple toggle 115 and plug 117 to each other and to portions of the artery to close the puncture. Filament 118 may be formed into a loop as shown in FIG. 1. Slideable knot 123 is formed from two portions of filament 118 being tied together to create such a loop. Filament 118 may be, for example, a braided multifilament size 2-0 PGA suture, but can also be made from any synthetic absorbable plastic material that degrades over time.

Closure device 150 also includes locking member 119. As shown in FIG. 1, filament 118 feeds through an opening/lumen in locking member 119. Locking member 119 is associated with filament 118 such that locking member 119 is frictionally engaged with filament 118. In other words, locking member 119 remains in place on filament 118 when no force is placed on the locking member, and only overcomes its frictional engagement with filament 118 in response to an application of force on the locking member 119. The locking member 119 comprises, for example, a cylindrical piece of resorbable iron and/or stainless steel. The locking member 119 may be crimped in a manner to provide the frictional engagement/resistance to movement along the filament 118. However, the lock may not be present, and instead, the filament is looped and/or suturing is utilized to hold the relative locations of the elements of the closure device (e.g., plug 30 and toggle 30).

Embodiments of the present technology will now be described with respect to exemplary large bore procedures that include the referenced closure and deployment devices. In order to perform any of the related procedures, the user gains percutaneous access to, for example, the femoral artery, causing a puncture in the artery. To gain percutaneous access to the artery, the Seldinger technique may be used. For example, a hollow bore needle (not shown) is inserted into the artery. A guidewire is advanced through the hollow needle shaft and into the femoral artery a sufficient distance to allow removal of the needle without the guidewire pulling out of the vessel. Removing the needle leaves the guidewire in place, with a portion thereof extending into the artery. The guidewire, extending from outside the patient into the femoral artery, provides for an entry means for other medical devices. Therefore, once the guidewire is positioned in the vessel of the patient, catheters, or introducers, of gradually increasing diameters are advanced over the guidewire and through the puncture into the artery to further open the puncture site. Then, an introducer/procedure sheath set, i.e. an introducer inside an access tube or sheath, is provided via the guidewire such that the sheath runs through the artery puncture and, once positioned, provides for sizable access to the vessel interior from outside the body.

After the relevant procedure is completed, the puncture in the artery created by the bore needle during percutaneous access of the artery may be closed. An efficient method for large bore puncture closure that minimizes blood loss is desirable. For example, closure device 150 may be used to seal the puncture. FIGS. 2-10 show schematic views of closure device 150 during the process of closing a percutaneous puncture in an artery wall.

Figure 2:
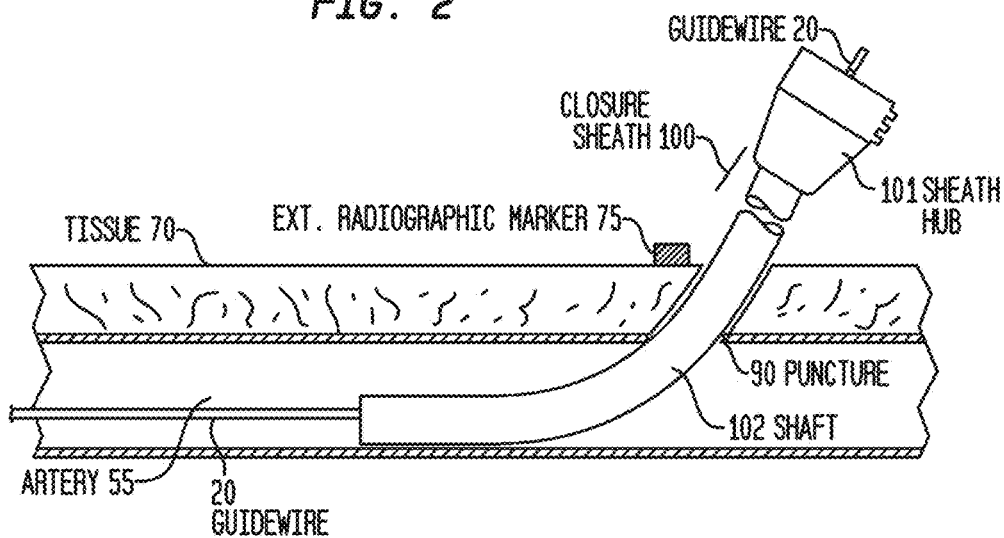
FIGS. 2-10 show schematic views of a closure device during the process of closing a percutaneous puncture in an artery wall, according to embodiments of the present technology.

To deliver closure device 150 to the puncture so that the closure device 150 may close the puncture, the introducer/procedure sheath set is replaced by a closure sheath set. For example, as shown in FIG. 2, closure sheath 100 is provided into artery 55 such that shaft 102 of sheath 100 runs through the artery puncture 90, providing access to the inside of artery 55. Procedure sheath is exchanged for the closure sheath by removing procedure sheath from the patient, leaving the guidewire in place, and feeding the closure sheath 100 over guidewire 20 into artery 55 through puncture 90. Closure sheath 100 remains partially within artery 55, partially within puncture 90, and partially outside artery 55, as shown in FIG. 2.

Figure 3:
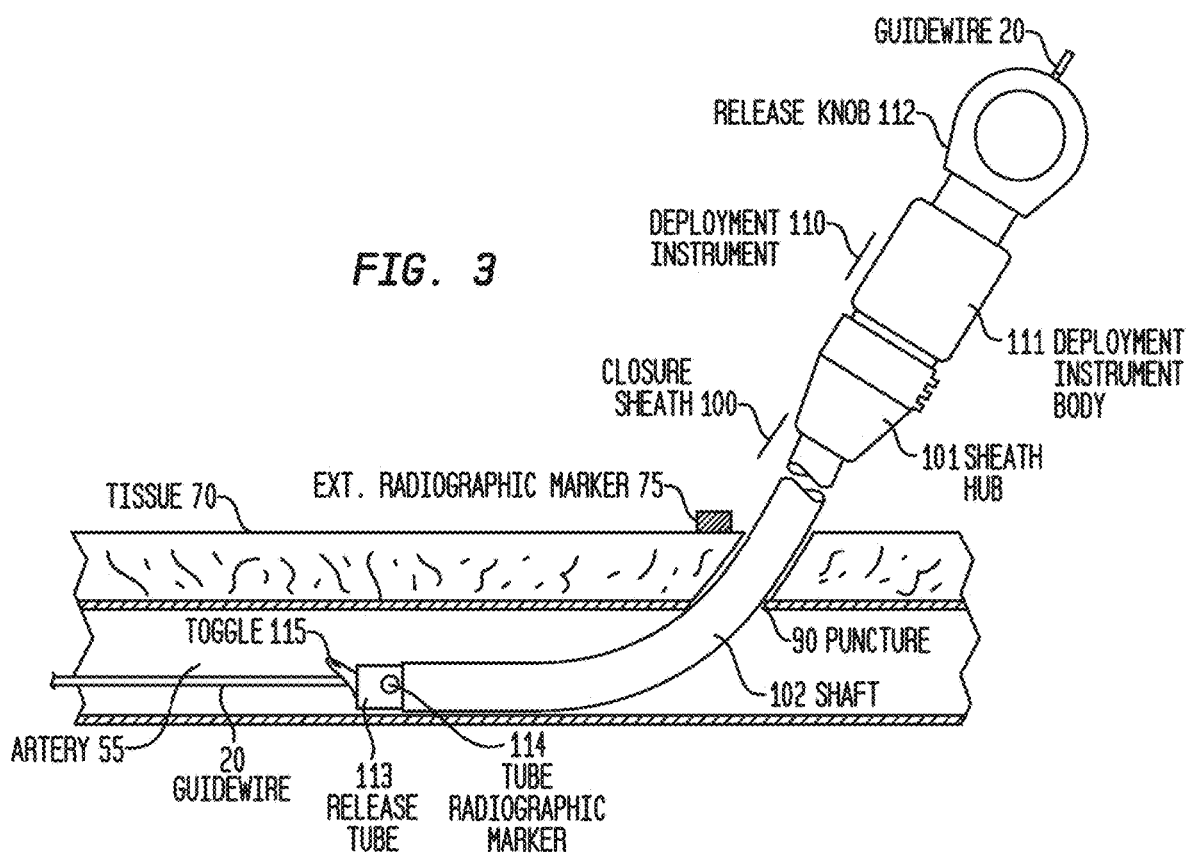

In order to seal a percutaneous puncture in an artery such as puncture 90, the deployment device 151, which contains closure device 150 within the hollow inside portion (not shown) of deployment device 151, gains access to the artery through the puncture. Deployment device 151 gains access to the artery via sheath 100, as shown in FIG. 3. Sheath 100 includes a hub 101 and a shaft 102. Sheath hub 101 is connected to sheath shaft 102 on one end of hub 101, and is configured to receive deployment instrument 151 at its other end. Sheath hub 101 is specifically designed to interface with the deployment instrument body 111 (also, for example, the handle of the deployment instrument). In FIG. 3, deployment instrument body 111 is shown fully inserted into sheath 100 and attached (for example, snapped into) sheath hub 101.

Figure 5:
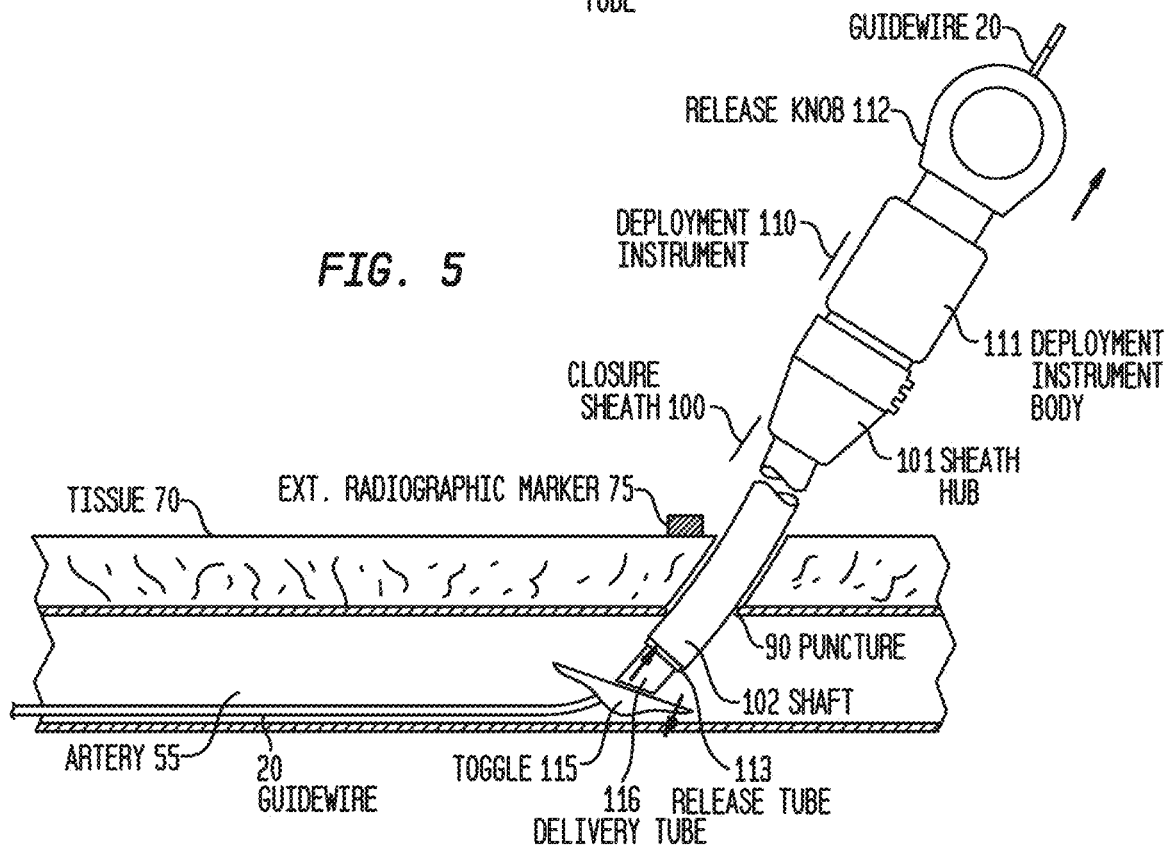

After deployment instrument 151, and therefore closure device 150, is in a desired location within artery 55, the user may release closure device 150 from deployment instrument 151. FIG. 3 shows the beginning of the process of releasing closure device 150 from deployment instrument 151. Shown protruding out of the distal end (the end within artery 55) of shaft 102 is a portion of closure device 150, including toggle 115 and release tube 113. As shown in FIG. 5, closure device 150 also includes delivery tube 116. Delivery tube 116 has a smaller diameter than release tube 113 such that release tube 113 can slide over delivery tube 116 as shown in FIG. 5. Toggle 115 is held within delivery tube 116 until released into artery 55.

Figure 4:
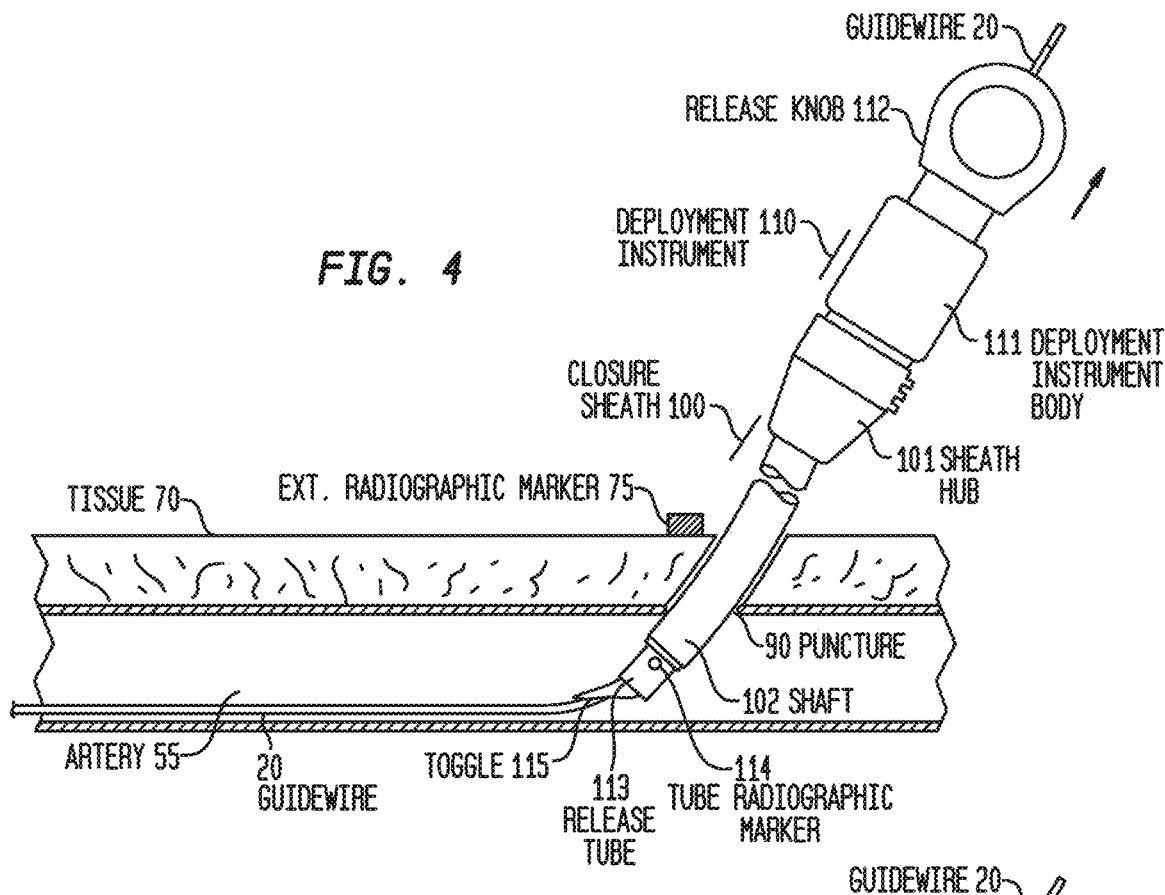
Figure 6:
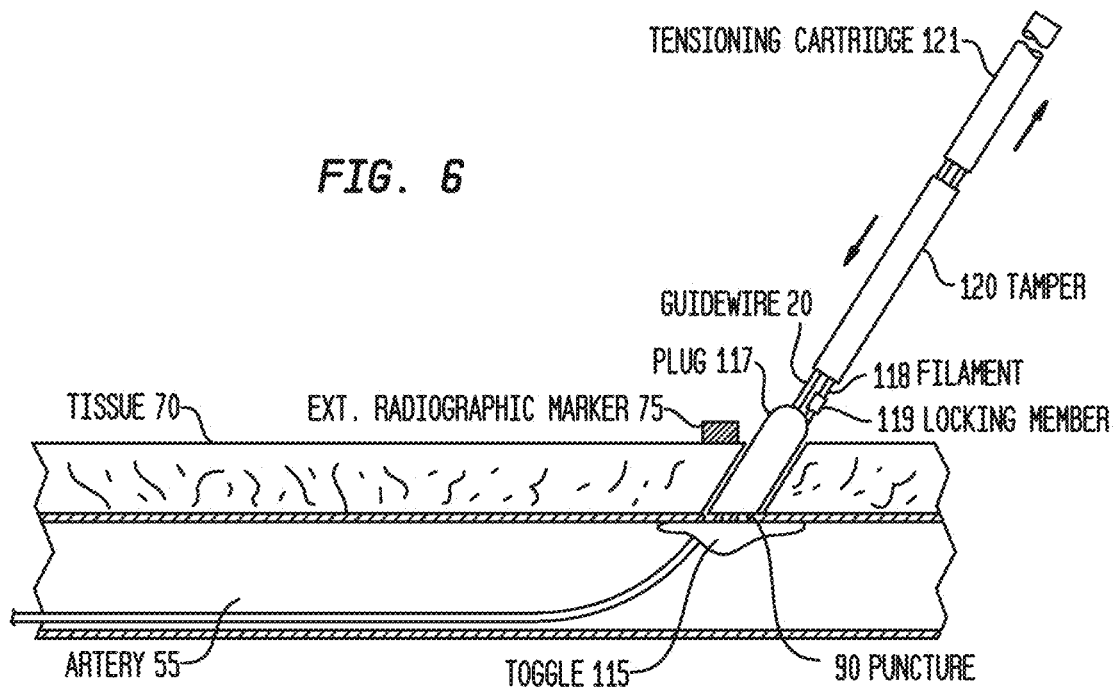

Before toggle 115 is released further from release tube 113, the entire device (including sheath 100, closure device 150, etc.) is gradually withdrawn from artery 55 until radiographic marker 114, which is located on release tube 113, aligns with external radiographic marker 75, as shown in FIG. 4. Radiographic marker 75 is located on the outside wall of artery 55 (e.g., on tissue 70 adjacent to puncture 90). This action places the toggle 115, as shown, in near proximity of the puncture 90. Release tube 113 is physically connected to release knob 112, whereby a pulling motion on the release knob 112 in a direction away from artery 55 moves the release tube 113 in the same direction. This pulling motion releases the toggle 115 out of release tube 113 and delivery tube 116 such that the toggle has an orientation substantially parallel with the longitudinal axis of vessel 55, as shown in FIG. 5. Given the proximity of the toggle 115 in relation to the puncture 90, further withdrawal of the combined assembly serves to move the toggle 115 into position on the inside surface of the vessel 55 at the puncture site 90, as shown in FIG. 6.

Figure 7:
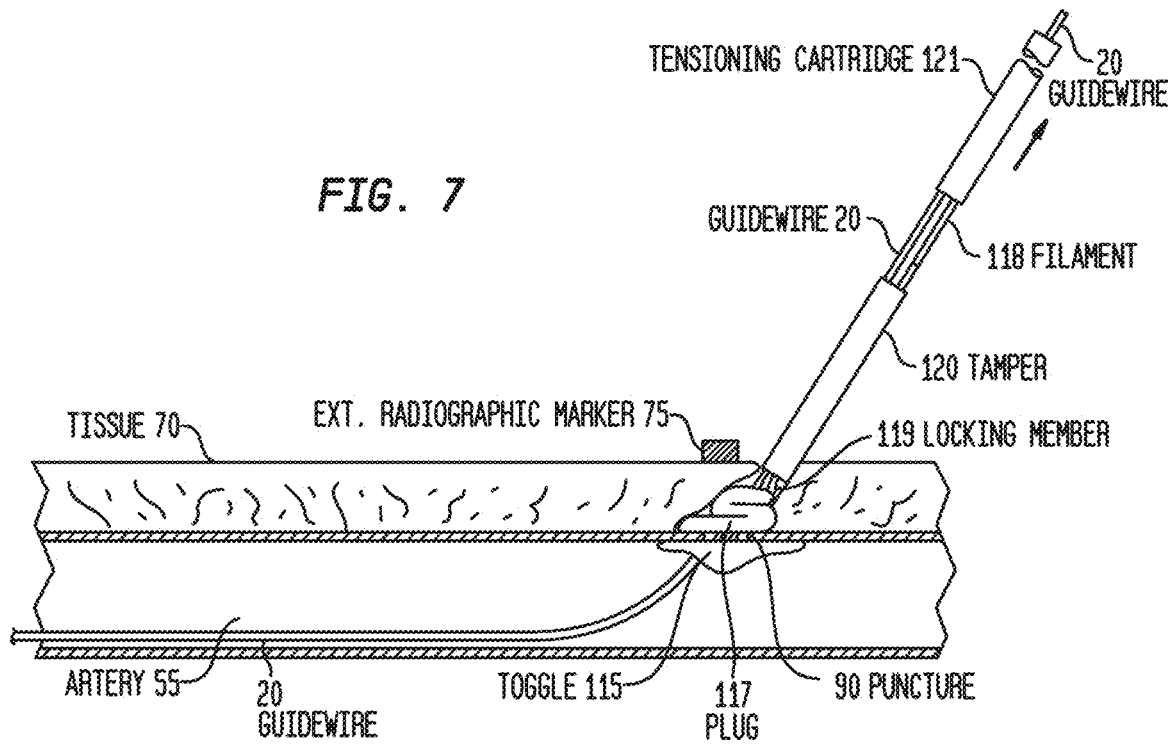

As the user further withdraws the closure device and connected sheath, the components within the delivery tube 116 emerge. FIG. 6 shows closure device 150, including toggle 115, plug 117, tamper 120, locking member 119, filament 118 and tensioning cartridge 121, fully withdrawn from deployment instrument 151 (not shown). As noted, toggle 115 and plug 117 are connected by a filament 118. In one embodiment, plug 117, toggle 115 and filament 118 are arranged in a pulley-like fashion. Therefore, pulling on tensioning cartridge 121 in a direction away from artery 55 (similar to the direction that release knob 113 was pulled to release the closure device elements) causes tension in filament 118 that moves toggle 115 fully into position against the inside wall of vessel 55 at puncture 90 such that toggle 115 covers puncture 90. Furthermore, the tension in filament 118 also pulls plug 117 into puncture 90, and causes plug 117 to fill out substantially the rest of the space within puncture 90, as shown in FIG. 7. As noted, after plug 117 is in contact with blood or other fluids within puncture 90, plug 117 will expand to fill out the rest of puncture tract 90.

Figure 10:
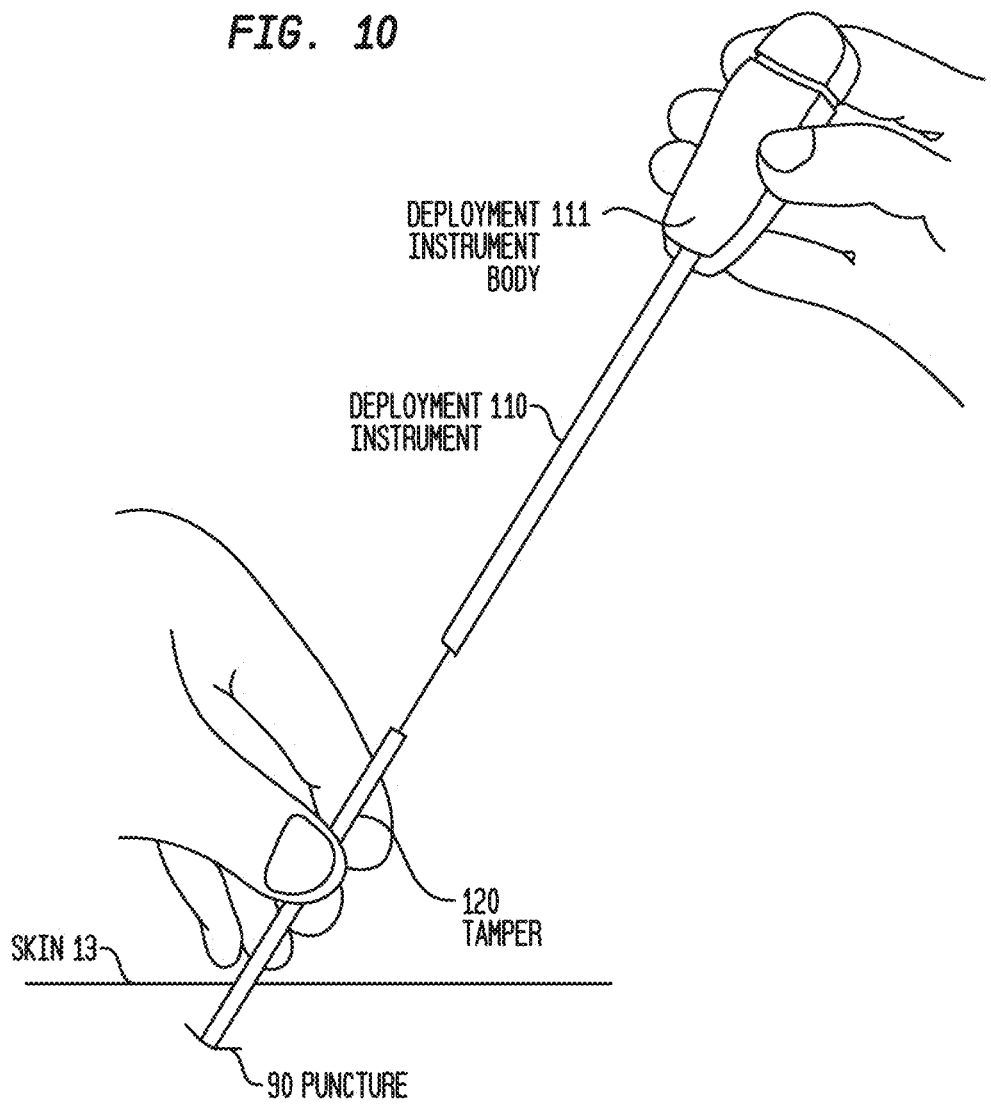

As noted, locking member 119 is associated with filament 118 such that locking member 119 is frictionally engaged with filament 118. In other words, locking member 119 remains in place on filament 118 when no force is placed on the locking member, and only overcomes its frictional engagement with filament 118 in response to an application of force on the locking member 119. After the user has pulled the tensioning cartridge 121 to cause tension in filament 118 and to cause plug 117 to enter puncture 90, the user advances tamper 120 along guidewire 20 and filament 118, as shown in FIG. 10, such that tamper 120 contacts locking member 119 and advances locking member 119 until locking member 119 contacts plug 117, as shown in FIG. 7. As also shown in FIG. 7, plug 117 folds over the top of and inside puncture 90. For example, as shown in FIG. 7, tamper 120 may push a portion or all of plug 117 below the outside surface of tissue/skin 70. Furthermore, tamper 120 may be inserted less than 1 cm into puncture 90, or may be inserted much greater distances (e.g. 3-6 cm, or more) into the puncture.

Figure 8:
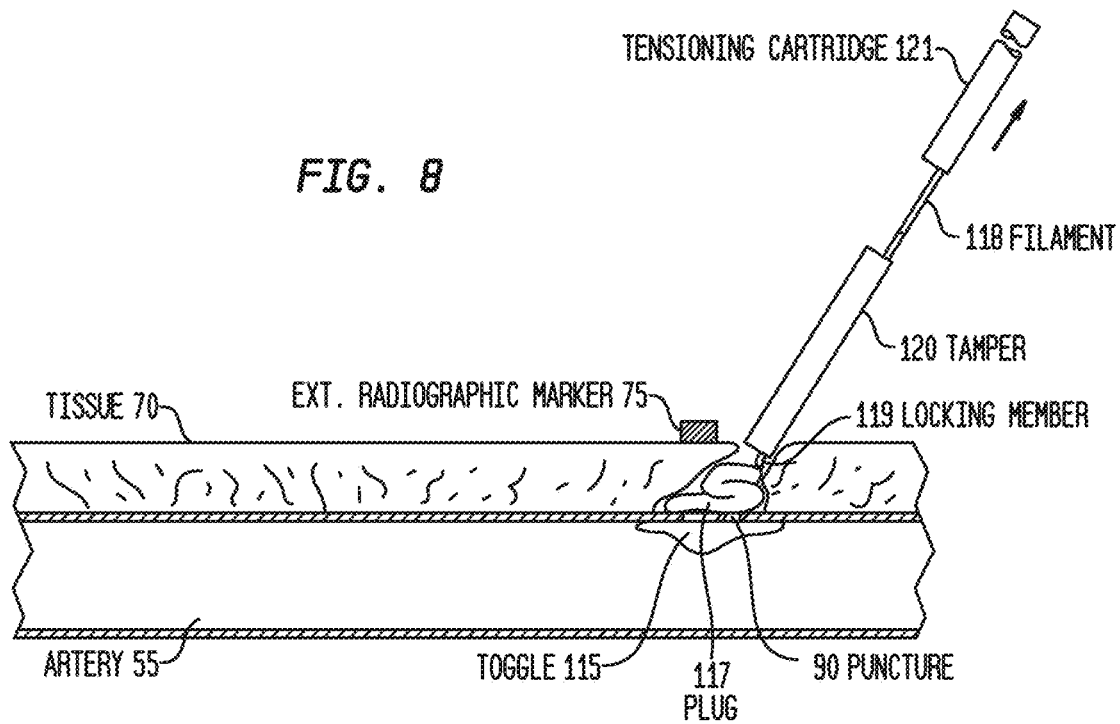
Figure 9:
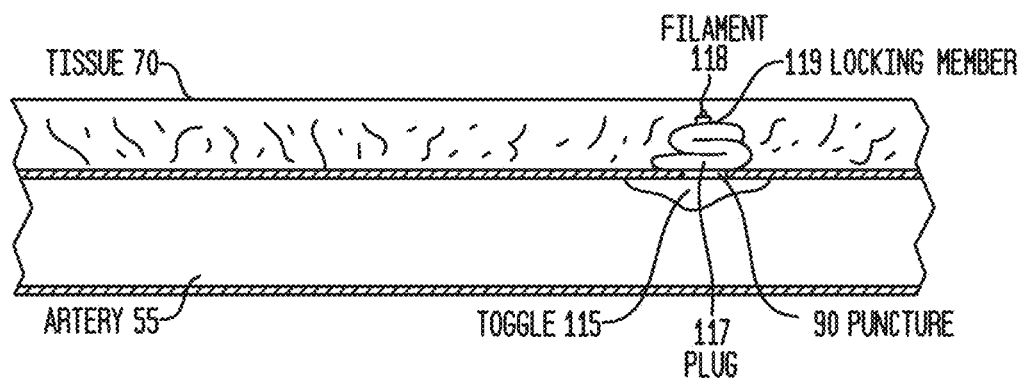

Locking member 119, together with the plug 117 and toggle 115, effect a seal of the puncture 90. As shown in FIGS. 8 and 9, tension is maintained on the tensioning cartridge 121 throughout the deployment of the plug 117 and toggle 115. After advancement of locking member 119 by the tamper tube 120 and folding/compaction of plug 117, guidewire 20 may be removed from the patient as shown in FIG. 8. Tension is still held on the tension cartridge 121, and the user may re-compress plug 117 as necessary to confirm a proper seal of puncture 90. After locking member 119 has secured plug in place and guidewire 20 has been removed, filament 118 may be cut below tamper 120 to remove the remaining filament 118, tamper 120 and tensioning cartridge 121 from the puncture site, as shown in FIG. 9. Remaining portions of closure device 150, including toggle 115 and plug 117, and a portion of filament 118, will resorb into the body of the patient over time (as may locking member 119, depending on the material making up locking member 119).

As noted, tamper 120 includes lumen that guidewire 20 and filament 118 feed through. Tamper 120 may include, for example, two lumens, three lumens, or more than three lumens. Referring back to FIG. 1, tamper 120 is shown as including three lumens, at least one lumen to receive guidewire 20 and at least one lumen to receive filament 118. The third lumen may be used to facilitate the delivery of pharmaceutical agents, such as thrombin, or other substances to the puncture. If tamper 120 includes less than three lumens, for example, either guidewire 20 or filament 118 may share the same lumen as a pharmaceutical agent.

Figure 11:
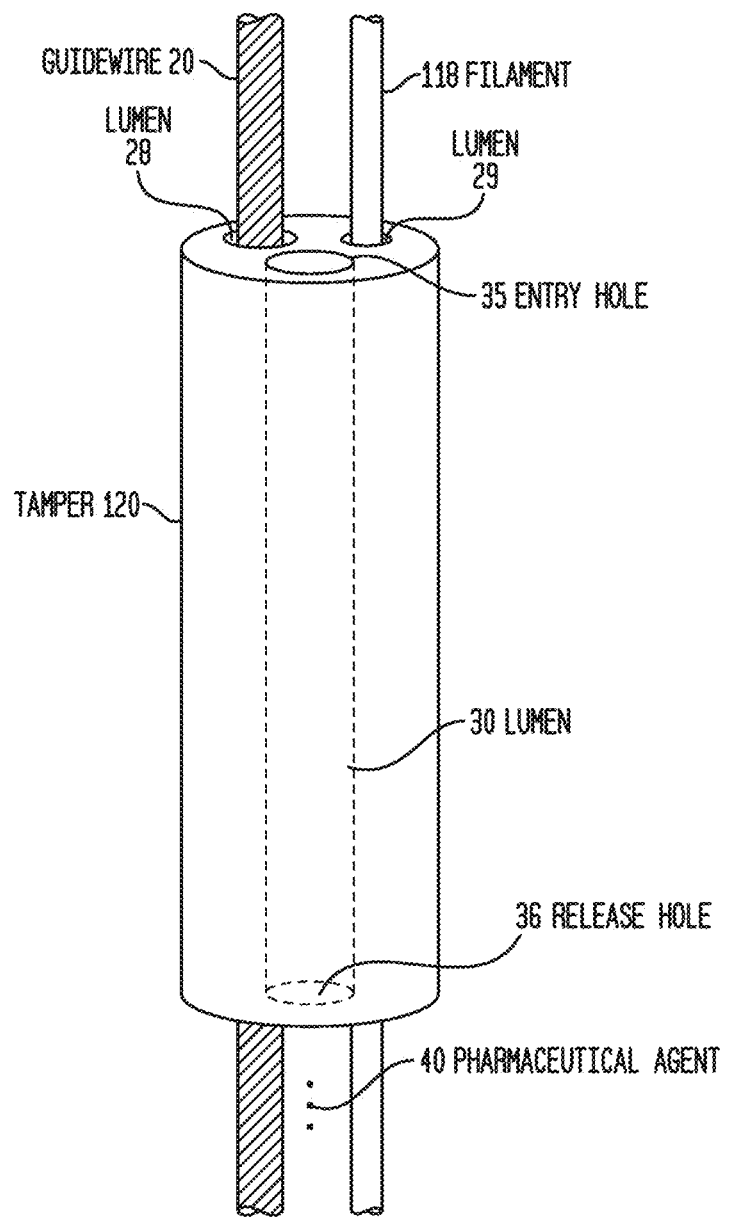
FIG. 11 shows a three-lumen tamper tube configured to deliver a pharmaceutical agent or other substance to a puncture site, according to embodiments of the present technology.

FIG. 11 shows a three-lumen tamper tube configured to deliver a pharmaceutical agent (i.e. drugs) or other substances to the puncture site, according to embodiments of the present technology. Tamper 120 includes lumen 28, through which guidewire 20 feeds, lumen 29, through which filament 118 feeds, and third lumen 30, which includes entry hole 35 into which a substance may be delivered. Third lumen 30 includes entry hole 35 located at the end of third lumen 30, and at the end of tamper 120, which may be at the distal end of tamper 120. It should be appreciated that the end of tamper 120 may be in a configuration other than flat (slanted, ridged, etc.). Furthermore, it should be appreciated that tamper 120 itself may be in a configuration other than an elongate cylindrical structure (rectangular box, shorter non-elongate cylinder, etc.). Third lumen 30 also includes release hole 36 located at the end of third lumen 30, and at the end of tamper 120, which may be closest to the artery wall. However, in certain embodiments, tamper 120 may be reversed such that hole 36 may be used as the entry point for substance delivery and hole 35 may be used as the release point for substance delivery.

The three (or more) lumens of tamper 120 may be any size or shape as long as the size of the lumen as a whole do not compromise the structural stability of tamper 120. For example, although lumen 28, 29 and 30 are shown in FIG. 11 as having a cylindrical shape, the lumen may be of a variety of different shapes. Furthermore, the lumen may have a larger diameter than the diameters shown in FIG. 11. For example, one or more of the lumens may have diameters stretching closer to the outside edge of tamper 120, and/or stretching closer to the other lumen. However, as noted, the lumen should not have diameters such that the structural stability of tamper 120 is compromised. For example, if one or more of the tamper lumen were wide enough, then a user holding the tamper and, for example, applying force on the tamper with the user's fingers, may damage tamper 120 by applying that force. On the other hand, the three lumens should be large enough to allow for the unrestricted movement of guidewire 20, suture 118 and/or pharmaceutical agent 40 through the lumen within tamper 120 (unless, for example, a certain level of restriction/friction/tension is desired).

Figure 12:
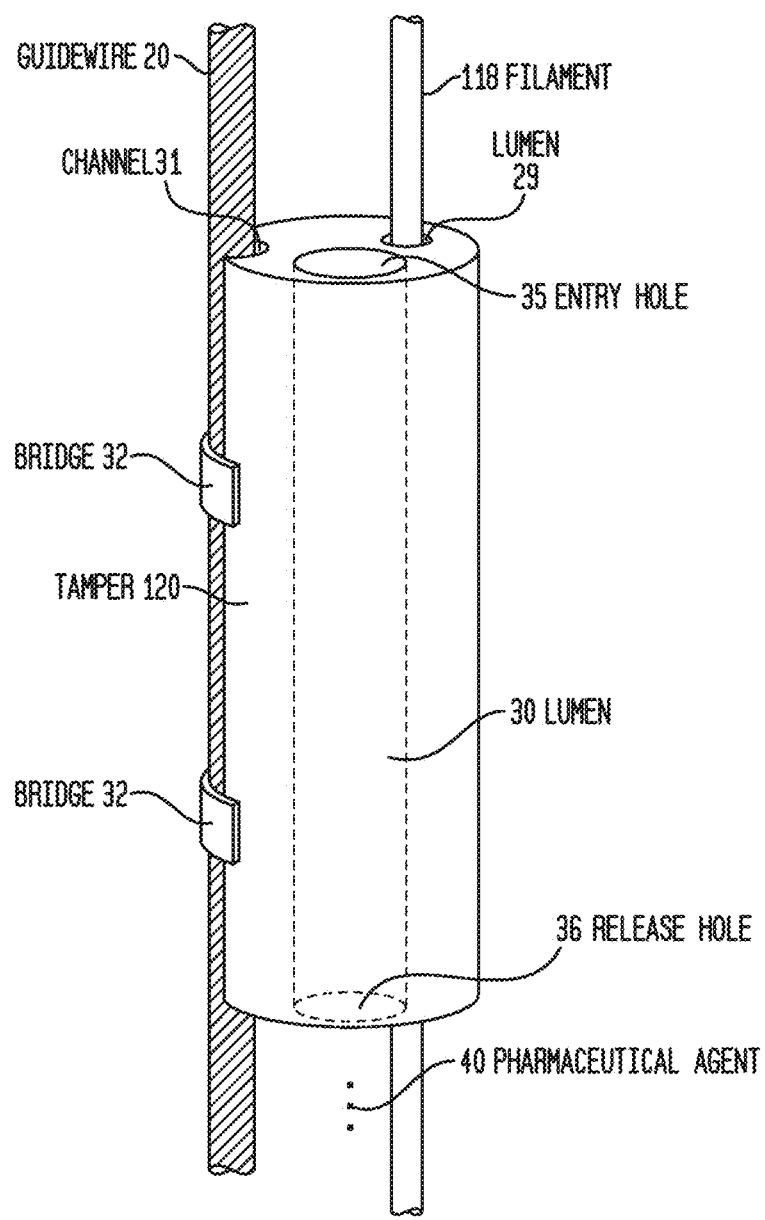
FIG. 12 shows a three-lumen tamper tube configured to deliver a pharmaceutical agent or other substance to a puncture site with a guidewire channel, according to embodiments of the present technology.

Furthermore, one or more of lumen 28, 29 and 30 may be located at the edge of tamper 120 such that the lumen is an elongate channel and includes an opening where the lumen is accessible from the exterior of tamper 120, as shown in FIG. 12. However, it may not be beneficial to the user for the user's fingers to touch the contents of the channel 31, such as guidewire 20, filament 118, or agent 40. Therefore, the channel may be configured in such a way (skinny in width, small opening, etc.) that prevents the fingers of the user from penetrating the lumen. Furthermore, tamper 120 may include bridges 32 attached to the body of the tamper that allow for the user to touch portions of the channel's surface area, but without penetrating the internal portions of channel 31. The bridges may also have further utility in that they may cause the guidewire, suture, or agent to be "trapped" or otherwise retained within the channel (if, for example, the configuration of the channel does not already have that utility).

As noted, tamper 120 contacts locking member 119 and advances locking member 119 until locking member 119 contacts plug 117, as shown in FIGS. 7 and 8. Since the distal end of tamper 120 contacts locking member 119, the holes in that end of tamper 120 should not be large enough such that locking member 119 (or plug 117) may be pushed into the lumen in tamper 120 connected to that hole. This size requirement for release hole 36, for example, is therefore dependent on the size of the proximal end of locking member 119 that is used in the relevant embodiment of closure device 150.

In some embodiments, it may be beneficial for one or more of the lumen, such as the lumen configured to deliver a pharmaceutical agent, to have a diameter as large as possible so that it may carry the largest amount of pharmaceutical agent as possible as one time for delivery to the puncture site. For example, in one embodiment of tamper 120, the walls between lumen 30 and the other lumen may be very thin so as to only prevent pharmaceutical agent 40 from exiting lumen 30 before reaching release hole 36. However, the walls between the lumen should not be so thin such that, either guidewire 20 or suture 118 may puncture one or more of the walls. Furthermore, the drug delivery lumen may have a specifically chosen size such that a drug may be delivered at a certain predetermined rate.

Figure 13:
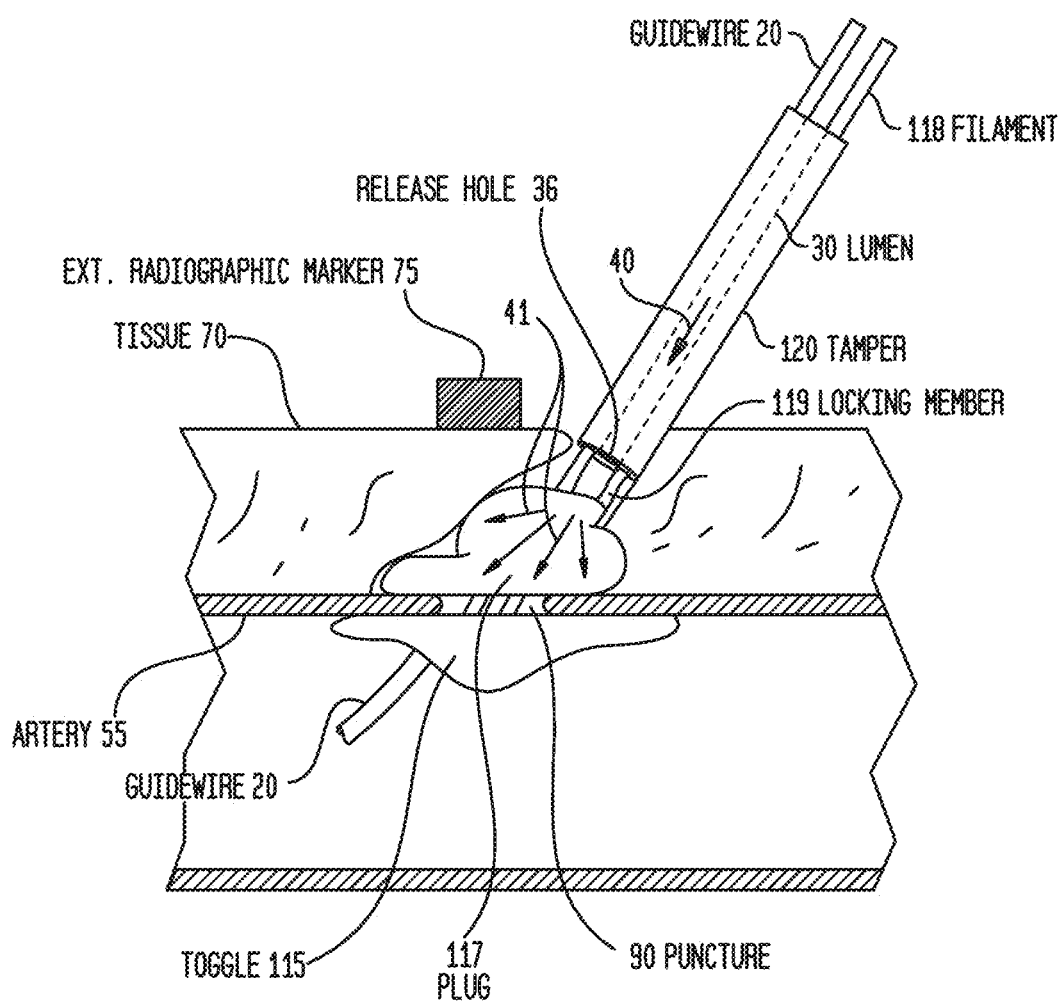
FIG. 13 shows a three-lumen tamper configured to deliver a pharmaceutical agent or other substances to the puncture site, including a plug, according to embodiments of the present technology.

FIG. 13 shows a three-lumen tamper 120 configured to deliver a pharmaceutical agent or other substances to the puncture site, including plug 117, according to embodiments of the present technology. More specifically, FIG. 13 shows the flow of the pharmaceutical agent, or other substance, through lumen 30, as shown by arrow 40, and into plug 117, which is at least partially condensed into puncture 90, as shown by arrows 41. Tamper 120 is fed over guidewire 20 because guidewire 20 allows for the guided motion of tamper towards and away from the puncture site when desired by the user. In other words, guidewire 20 prevents the user from having to balance tamper 120 on locking member 119 and/or plug 117 in the lateral direction (the direction perpendicular to a longitudinal axis going through tamper 120 from the distal end of the tamper to the proximal end). Third lumen 30 allows for a similar guided path for a pharmaceutical agent or other substance to follow through tamper 120, as well as a guided (predetermined) delivery point of release hole 36. If no guidewire is used in closure device 150, suture 118 may serve the same purpose as guidewire 20, namely to provide for a guided path for the pharmaceutical agent or other substance to be delivered to the puncture/plug. In other words, because lumen 30 is substantially parallel to lumen 28 and lumen 29, a substance deposited into lumen 30 will travel in the same direction as guidewire 20 and/or filament 118, allowing the user to control the location of deposit of the substance through release hole 36 based on the location of guidewire 20 and/or filament 118. It should be appreciated that even if two or more of lumen 28, 29 or 30 are not parallel but are close to being parallel, such an embodiment was contemplated by the inventors. Lumen 30 allows for the user to deliver a pharmaceutical agent or another substance to a specific desired location within the surgical site, such as onto plug 117 or elsewhere. This goal of delivery of a pharmaceutical agent or another substance to a specific desired location within the surgical site is achieved if the user understands the physical relationship between the pharmaceutical delivery lumen and the other lumen.

The pharmaceutical agent 40 deposited into lumen 30 via entry hole 35 may include any of many different drugs such as, for example, thrombin. Punctures/ruptures in arterial walls trigger the clotting cascade, a complex series of signals and protein activations that ultimately result in a clot to help close the puncture in the artery wall. The key factor in the clotting cascade is thrombin. Thrombin is a protease that, for example, activates platelets to form an initial "plug" of the puncture and conversion of fibrinogen to fibrin. Fibrin is responsible for forming a more permanent seal of the puncture and polymerizes to form a linked structure. Thrombin also activates Factor XIII to Factor XIIIa, which strengthens the bonds between the fibrin monomers in the linked structure, making the initial clot more permanent. Therefore, the inventors have discovered that accurate delivery of extra thrombin to the puncture site of a catheter procedure shortens the time to hemostasis.

Figure 14:
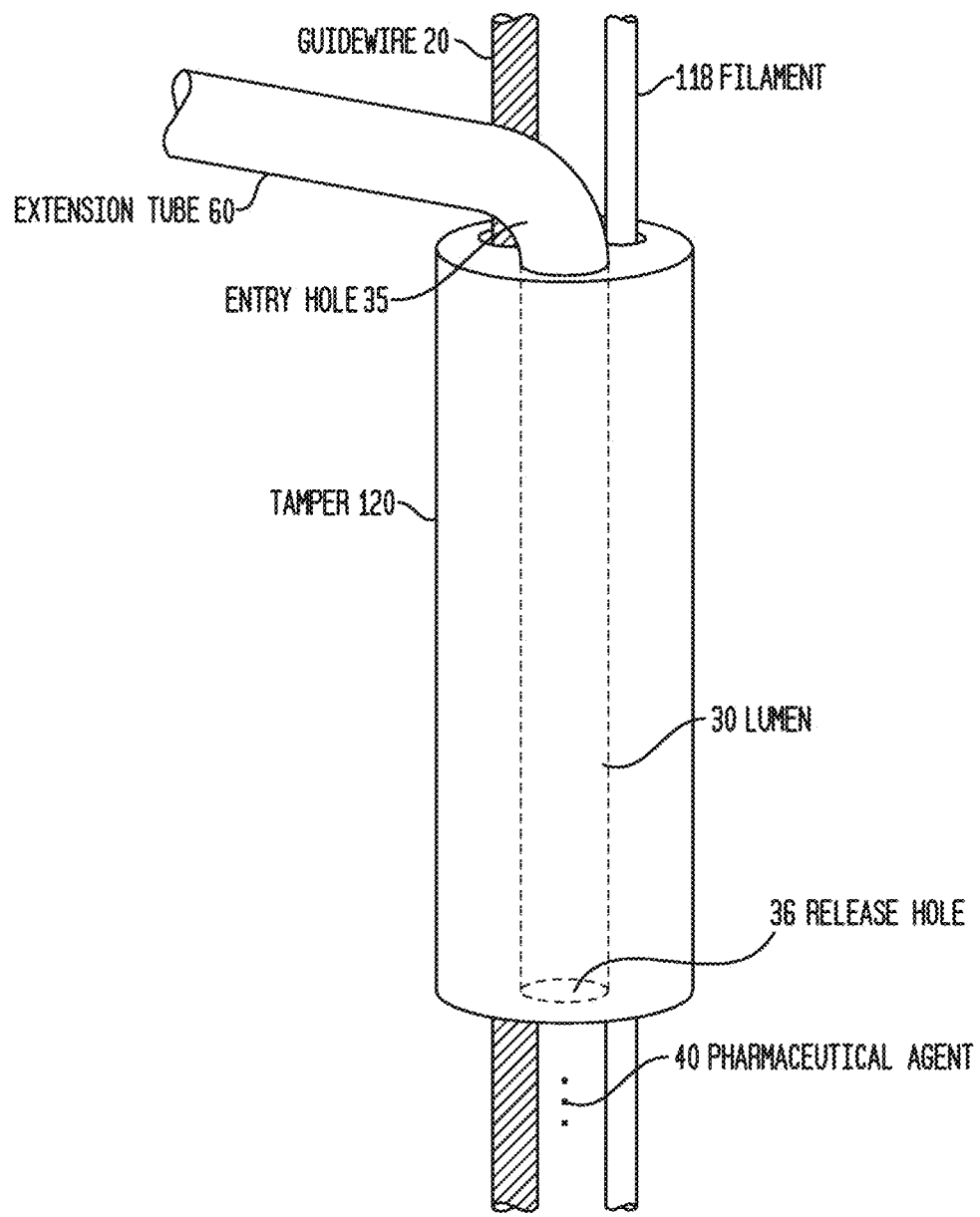
FIG. 14 shows a three-lumen tamper configured to deliver a pharmaceutical agent or other substances to the puncture site via a lumen and an extension tube, according to embodiments of the present technology.

FIG. 14 shows a three-lumen tamper 120 configured to deliver a pharmaceutical agent or other substances to the puncture site via lumen 30 and extension tube 60, according to embodiments of the present technology. Extension tube 60 is connected and sealed to entry hole 35 of lumen 30. Extension tube 60 allows for modified access to lumen 30. For example, extension tube 60 may allow for the user to insert a pharmaceutical agent or other substance into lumen 30 from outside the patient's artery, or from outside the patient all together. Extension tube 60 is shown in FIG. 14 as having a cylindrical, bent shape. However, extension tube 60 may have a variety of shapes and lengths and may vary in shape and/or length throughout its structure.

Figure 15:
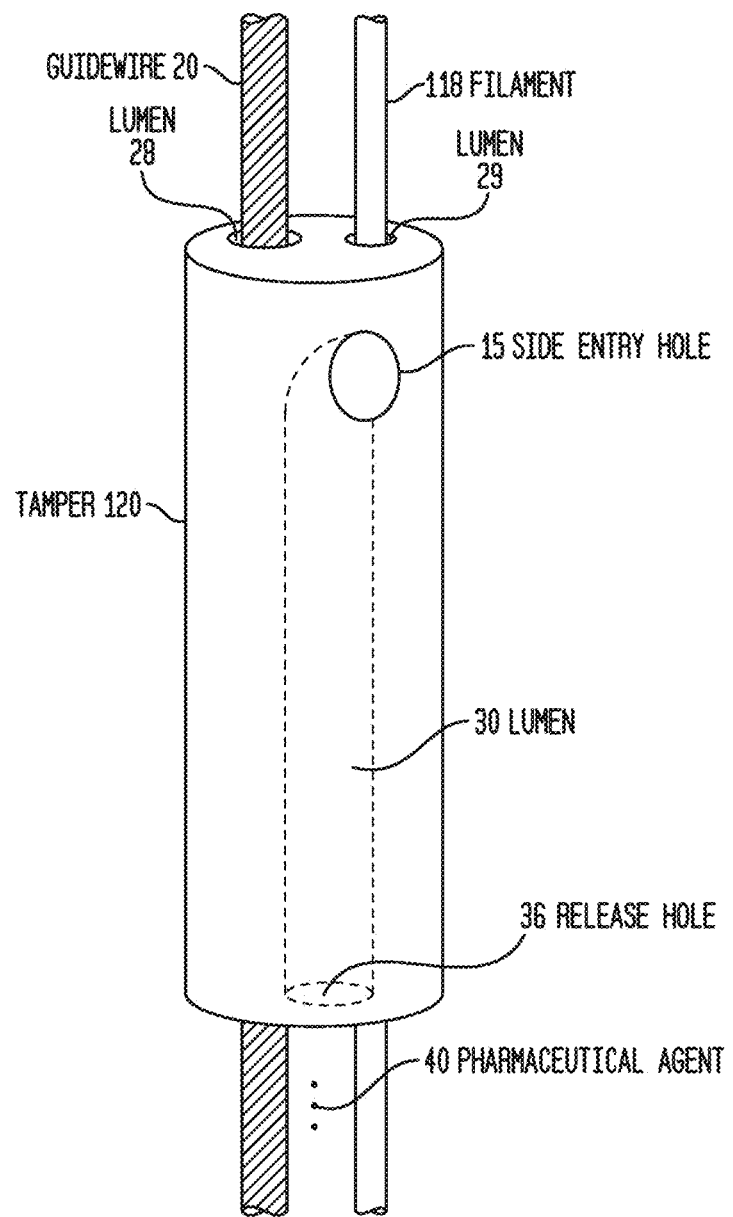
FIG. 15 shows a three-lumen tamper tube configured to deliver a pharmaceutical agent or other substance to the puncture site with an entry hole on the side of the tamper, according to embodiments of the present technology.

FIG. 15 shows a three-lumen tamper tube configured to deliver a pharmaceutical agent (i.e. drugs) or other substances to the puncture site with an entry hole on the side of tamper 120, according to embodiments of the present technology. While FIG. 11 included an embodiment of tamper 120 such that entry hole 35 is located at the end of tamper 120, entry hole 35 may also be placed on the side of tamper 120, as shown by side entry 15 in FIG. 15. Furthermore, tamper 120 may include an entry hole on any other portion of tamper 120 where the entry hole connects to lumen 30 to deliver inserted agents to the user's desired location. Placement of an entry hole at a variety of different portions of tamper tube 120 allows for the user to choose the location easiest for delivering the desired substance based on the user's desired delivery device. Furthermore, tamper 120, and more specifically one or more lumen of tamper tube 120, may include more than one access hole (such as entry hole 35 or side entry 15).

Figure 16:
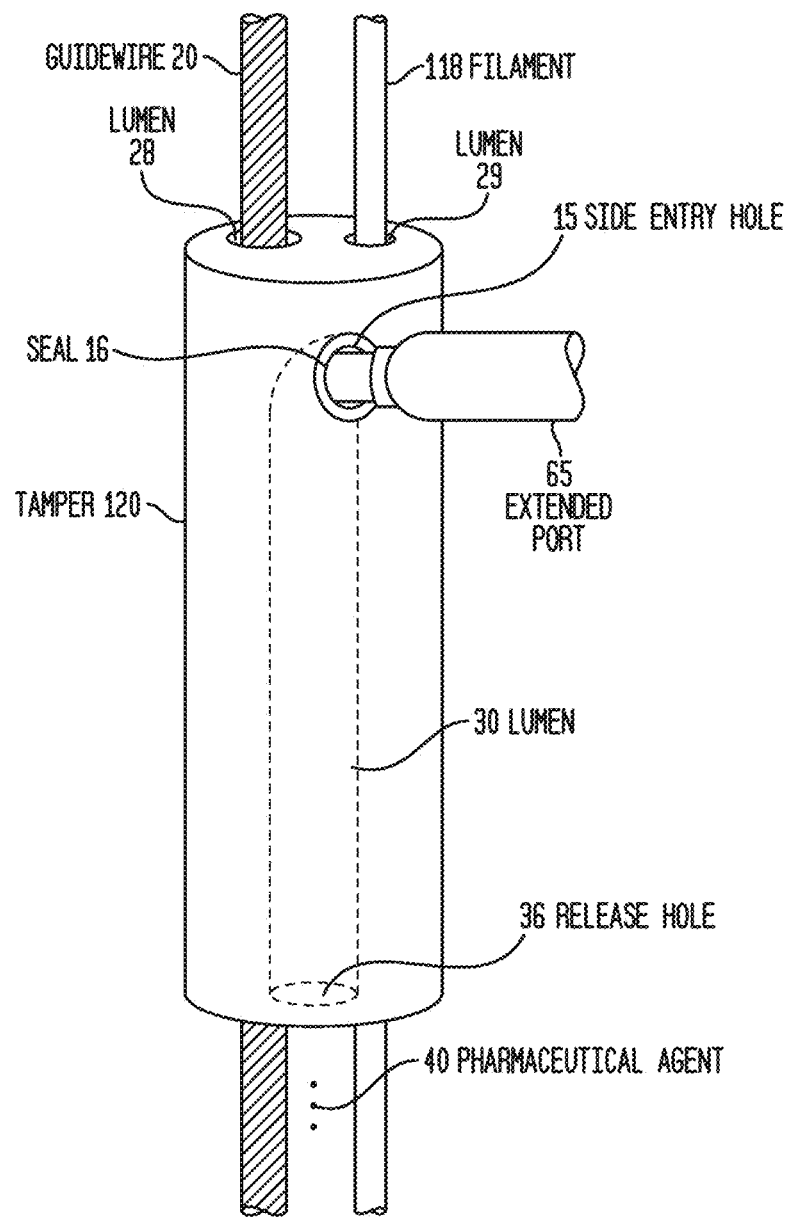
FIG. 16 shows a three-lumen tamper tube configured to deliver a pharmaceutical agent or other substance to the puncture site with an entry hole on the side of the tamper via a lumen and an extension tube, according to embodiments of the present technology.
Figure 17:
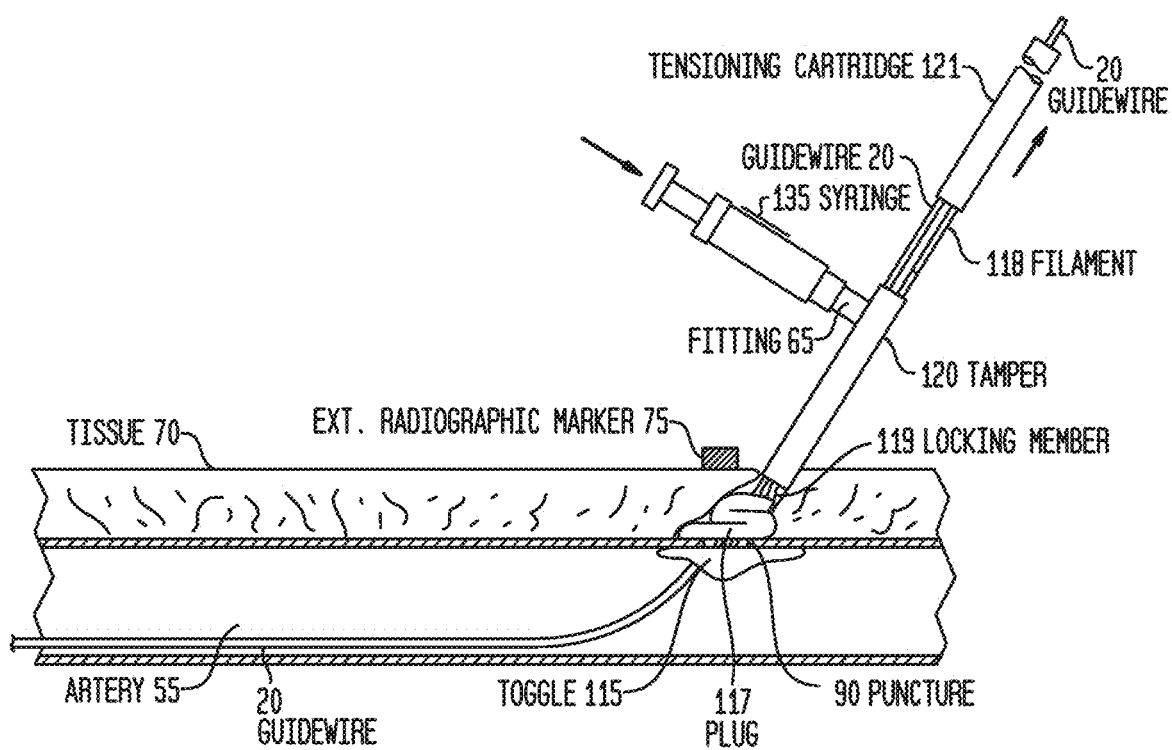
FIG. 17 shows a three-lumen tamper tube configured to deliver a pharmaceutical agent or other substance to the puncture site with an entry hole on the side of the tamper via a lumen and a drug delivery member, according to embodiments of the present technology.

Pharmaceutical agent 40 or other substance may be deposited into lumen 30 in a variety of different ways. For example, agent 40 may be deposited into lumen 30 using extended port 65, as shown in FIG. 16. A drug delivery member, such as a syringe, may be connected to the end of extended port 65 to deposit pharmaceutical agent into lumen 30 via extended port 65. Furthermore, a drug delivery member, such as syringe 135, may be connected directly to entry hole 15 without the use of extended port 65, as shown in FIG. 17. Extended port 65 is connected to entry hole 15, and may be sealed via seal 16 such that pharmaceutical agent deposited into hole 15 via port 65 is not leaked from the connection between port 65 and hole 15. The syringe or other deposit mechanism may be connected to tamper 120 in a variety of different ways, including a variety of different locations based on the location of the entry hole. For example, as noted, extension port 65 may be connected to an extension such as extension tube 60, or to any other mechanism that allows for the pharmaceutical agent or other substance to be safely deposited into lumen 30.

Furthermore, the pharmaceutical agent may be delivered via lumen 30, for example, at any time during the large bore closure procedure. For example, a pharmaceutical agent may be delivered to the puncture site before plug 117 has been condensed, after plug 117 has been partially condensed, after plug 117 has been fully condensed, or after plug 117 has been expanded to fill out the rest of puncture 90.

The technology described and claimed herein is not to be limited in scope by the specific preferred embodiments herein disclosed, since these embodiments are intended as illustrations, and not limitations, of several aspects of the technology. Any equivalent embodiments are intended to be within the scope of this technology. Indeed, various modifications of the technology in addition to those shown and described herein will become apparent to those skilled in the art from the foregoing description. Such modifications are also intended to fall within the scope of the appended claims.

What is claimed:

1. A vascular closure device configured to seal a percutaneous puncture in a wall of a body passageway, the vascular closure device comprising:
   a plug configured to engage a surface of the puncture;
   a suture coupled to the plug;
   a locking member coupled to and slidable along the suture; and
   a tamper slidably coupled to the suture at a location that is proximal to the locking member, the tamper having a proximal end, a distal end spaced from the proximal end along an axis, a first lumen that extends from the proximal end to the distal end along the axis, and a second lumen that extends from the proximal end to the distal end along the axis, wherein the first lumen and the second lumen each have a cross-sectional dimension that inhibits the locking member from being pushed inside either of the first and second lumens when the tamper slides along the suture to tamp the locking member against the plug.

2. The vascular closure device of claim 1, wherein the tamper is a cylindrical tube.

3. The vascular closure device of claim 1, wherein at least one of the first lumen and the second lumen is a channel that extends along at least a portion of an outer surface of the tamper.

4. The vascular closure device of claim 1, wherein the plug is a resorbable collagen sponge or foam.

5. The vascular closure device of claim 1, further comprising an extension tube connected to an access opening of the tamper; and a drug delivery member configured to deliver a pharmaceutical agent to the first lumen.

6. The vascular closure device of claim 1, wherein the tamper engages the locking member at the distal end of the tamper such that the tamper causes the locking member to contact and compress the plug.

7. The vascular closure device of claim 1, further comprising a toggle coupled to the suture and located distally with respect to the plug.

8. The vascular closure device of claim 1, wherein the suture extends through either of the first lumen or the second lumen.

9. The vascular closure device of claim 8, wherein the plug includes a first plurality of holes and a second plurality of holes, wherein the suture extends through a) the first plurality of holes, b) a hole in the toggle, and c) the second plurality of holes to form a slidable knot adjacent to the locking member.

10. The vascular closure device of claim 1, wherein the tamper includes a plurality of openings.

11. The vascular closure device of claim 1, wherein an entry hole is located at a distal end of the tamper.

12. The vascular closure device of claim 1, wherein a release hole is located at a proximal end of the tamper.

13. A drug delivery kit, comprising:
- a sealing unit configured to seal a percutaneous puncture in a wall of a body passageway, the sealing unit having a suture;
- a locking member coupled to the suture;
- a tamper slidably coupled to the suture at a location proximal to the locking member, the tamper having a proximal end and a distal end spaced from the proximal end along an axis, wherein the tamper has a first lumen that extends from the proximal end to the distal end along the axis and a second lumen that extends from the proximal end to the distal end along the axis, wherein the first lumen and the second lumen each have a cross-sectional dimension that inhibits the locking member from being pushed inside either of the first and second lumens; and
- a pharmaceutical agent releasably carried in at least one of the first lumen or the second lumen.

14. The drug delivery kit of claim 13, wherein the sealing unit further comprises a plug configured to engage the puncture of the body passageway.

15. The drug delivery kit of claim 14, wherein the tamper is configured to deliver the pharmaceutical agent to a desired location on the plug.

16. The drug delivery kit of claim 14, wherein the tamper is configured to slide along a guidewire, the guidewire is guided through a lumen of the tamper, and the guidewire is guided through an opening in the plug.

17. A deployment instrument, comprising:
- a sealing unit having a tamper slidably couplable to a suture at a location proximal to a locking member coupled to the suture, the tamper having a proximal end and a distal end spaced from the proximal end along an axis, wherein the tamper comprises at least two lumens that extend from the proximal end to the distal end of the tamper along the axis, and each of the at least two lumens has a cross-sectional dimension that inhibits the locking member from being pushed inside either of the at least two lumens, the sealing unit configured to transition from a pre-deployment state into a deployed state;
- a carrier device configured to a) hold the sealing unit in the pre-deployment state, b) cause the sealing unit to transition from the pre-deployment state into the deployed state.

18. The deployment instrument of claim 17, wherein at least one of the at least two lumens is a channel that extends along at least a portion of an outer surface of the tamper.

19. The deployment instrument of claim 17, further comprising an extension tube connected to an access opening of the tamper; and a drug delivery member configured to deliver a pharmaceutical agent to at least one of the at least two lumens.

20. The deployment instrument of claim 17, wherein the tamper engages the locking member at the distal end of the tamper such that the tamper causes the locking member to contact and compress a plug in the deployed state.

* * * * *